(12) United States Patent
Xie et al.

(10) Patent No.: US 11,970,830 B2
(45) Date of Patent: Apr. 30, 2024

(54) METHOD FOR QUANTIFYING BEARING CAPACITY OF FOUNDATION CONTAINING SHALLOW-HIDDEN SPHERICAL CAVITIES

(71) Applicant: HAINAN UNIVERSITY, Haikou (CN)

(72) Inventors: Peng Xie, Haikou (CN); Zurun Yue, Haikou (CN); Haijia Wen, Haikou (CN); Ying Teng, Haikou (CN); Shuqi Yang, Haikou (CN); Jiaqi Li, Haikou (CN); Lei Yan, Haikou (CN); Yuxuan Yang, Haikou (CN); Shaolong Jie, Haikou (CN); Bingyang Liu, Haikou (CN); Jingjing Fu, Haikou (CN); Jing Xie, Haikou (CN); Zhichao Du, Haikou (CN); Di Yin, Haikou (CN)

(73) Assignee: HAINAN UNIVERSITY, Haikou (CN)

( * ) Notice: Subject to any disclaimer, the term of this patent is extended or adjusted under 35 U.S.C. 154(b) by 641 days.

(21) Appl. No.: 17/186,499

(22) Filed: Feb. 26, 2021

(65) Prior Publication Data
US 2021/0285178 A1    Sep. 16, 2021

(30) Foreign Application Priority Data

Feb. 26, 2020   (CN) .......................... 202010118111.8

(51) Int. Cl.
*G01N 33/24*   (2006.01)
*E02D 1/00*    (2006.01)
*G06N 7/00*    (2023.01)

(52) U.S. Cl.
CPC ............... *E02D 1/00* (2013.01); *G01N 33/24* (2013.01); *G06N 7/00* (2013.01)

(58) Field of Classification Search
CPC . E02D 1/00; G01N 33/24; G06N 7/00; G06T 17/00
See application file for complete search history.

(56) References Cited

U.S. PATENT DOCUMENTS

2013/0151160 A1*   6/2013   Chertov .............. G01M 5/0066
                                                        702/11

* cited by examiner

*Primary Examiner* — Eric S. McCall
*Assistant Examiner* — Timothy P Graves
(74) *Attorney, Agent, or Firm* — Raj S. Dave; Dave Law Group LLC (57) ABSTRACT

The present disclosure discloses a method for quantifying a bearing capacity of foundation containing shallow-hidden spherical cavities, comprising: in Step 1, constructing a spatial axisymmetric calculation model for stability analysis of the foundation containing shallow-hidden spherical cavities; in Step 2, solving the model to obtain a general solution which reflects the spatial stress distribution of surrounding rock containing shallow-hidden spherical cavities; in Step 3, obtain a mathematical expression by derivation for calculating the bearing capacity of the foundation containing shallow-hidden spherical cavities; and in Step 4: completing the determination of the foundation bearing capacity. Benefits: This method has many advantages such as comprehensive consideration, high accuracy and reliability of calculation results, and may provide the scientific basis for the development of prevention and control against the instability of the foundation containing shallow-hidden cavities. This method is easy to operate and feasible to become popular in actual engineering projects.

4 Claims, 3 Drawing Sheets

METHOD FOR QUANTIFYING BEARING CAPACITY OF FOUNDATION CONTAINING SHALLOW-HIDDEN SPHERICAL CAVITIES

TECHNICAL FIELD

The present disclosure relates to a method for quantifying the bearing capacity of foundation, in particular to a method for quantifying the bearing capacity of foundation containing shallow-hidden spherical cavities.

BACKGROUND

China, one of the countries owning the most developed Karst in the world, has a distribution area of soluble rock up to $3.43 \times 10^6$ km$^2$, accounting for ⅓ of the total land area. Unlike distribution characteristics abroad, in the total area of $3.43 \times 10$ 6 km$^2$ of soluble rock, only $1.25 \times 10^6$ km$^2$ thereof is exposed, with the rest staying concealed. Due to the interaction between soluble rock and acidic water mass, hidden cavities will be formed in near-surface areas. City acts both as the carrier of society and the symbol of ongoing human civilization. Therefore, while China attaches great importance to the economic development, it is also steadily advancing the process of urbanization. In order to meet people's needs across the entire development, the engineering construction have been greatly improved in scale and speed, and the land occupation has been increasing. With the transformation of the land resource use and continuous development of disaster-prone regions, the foundation instability related to hidden cavities has become a common problem in practical engineering, which causes losses involving various aspects such as agricultural engineering, highway engineering, railway engineering, mining engineering, and industrial and civil construction engineering. Therefore, the prevention and control of disasters caused by foundation instability related to shallow-hidden cavities has become significant requirements for guaranteeing national security and social and economic development.

In order to better understand the connotation and extension of ground collapse disasters, scholars at home and abroad have carried out a great deal of researches, mainly focusing on qualitative and quantitative aspects. In terms of qualitative researches, researchers summarized the failure mechanism of ground collapse on the basis of laboratory tests and outdoor reconnaissance. With the development and progress of science and technology, interdisciplinary researches have been achieved thanks to more resource sharing, and ideas such as logistic regression and fuzzy theory have been introduced to establish a series of models for evaluating the susceptibility to ground collapse. In terms of quantitative researches, researchers mainly focus on the influence of hidden cavities on the stress distribution of surrounding rock, as well as quantitative indexes for foundation stability evaluation.

In conclusion, in order to better understand adverse effects of ground collapse, scholars have carried out extensive and in-depth researches, and achieved a plenty of results. As far as the quantitative research is concerned, this issue is generally transformed into a problem in a two-dimensional plane for solving, which takes neither spatial three-dimensional characteristics of shallow-hidden objects, nor the influences of external load, rock-soil mass dead-weight and virgin rock stress into comprehensive consideration. Therefore, by considering a combined effect of geometric characteristics of and complex stresses borne by hidden cavities comprehensively, those skilled in this art should consider to provide an accurate quantitative method of foundation bearing capacity.

SUMMARY

The present disclosure aims at getting better understanding of adverse effects brought by instability of the foundation containing shallow-hidden spherical cavities, and providing a method for quantifying the bearing capacity of foundation containing shallow-hidden spherical cavities.

The present disclosure provides a method for quantifying the bearing capacity of foundation containing shallow-hidden spherical cavities, including steps described as follows:

In Step 1, by comprehensively considering a combined effect of spatial three-dimensional characteristics of a shallow-hidden spherical cavity, a self-weight stress of an overlying rock-soil layer, a virgin rock stress, and an external vertical load, a spatial axisymmetric calculation model is constructed for stability analysis of the foundation containing shallow-hidden spherical cavities;

In Step 2, by selecting a spherical coordinate system and introducing the Laplace displacement method, the model is solved through theoretical analysis to obtain a general solution which reflects the spatial stress distribution of surrounding rock containing shallow-hidden spherical cavities;

In Step 3, by combining the genetal solution obtained through theoretical analysis in Step 2, a damage mode of ground collapse, and the Mohr-Coulomb strength theory, a mathematical expression for calculating the bearing capacity of the foundation containing shallow-hidden spherical cavities is derived;

In Step 4, by substituting data of a vertical load of stratum, a gravity density of a rock-soil layer, a Poisson's ratio of rock-soil mass, a thickness of an overlying stratum, and a radius of a spherical cavity that are measured in actual engineering projects into the mathematical expression in Step 3 for calculation, the bearing capacity of the foundation may be determined.

Various parameters and formulas in the spatial axisymmetric calculation model in Step 1 are as follows:

$p_z$—external load borne by the ground;
$p_0$—horizontal load of virgin rock stratum, $p_0 = \mu[p_z + \gamma(h+z)]/(1-\mu)$;
$\gamma$—gravity density of rock-soil layer, in kN·m;
$\mu$—Poisson's ratio of rock-soil mass;
h—thickness of overlying stratum, in m;
R—distance from any point to spherical cavity center, in m.

The calculation formulas of the general solution in Step 2 are as follows:

$$\sigma_R = \{4[16(1-\mu)A_2 - A_4]\sin^2\varphi\cos\varphi + 8[(2-\mu)A_4]\cos^3\varphi\}R + \quad (1.1)$$
$$\{2[3\mu A_3 + (2\mu-1)A_5]\sin^2\varphi + 22[(1-\mu)A_3 + 2(2-\mu)A_5]\cos^2\varphi\} +$$
$$A_9[15\cos^6\varphi + 15\sin^4\varphi\cos\cos^2\varphi + 30^2\varphi\cos^4\varphi - 3\sin^4\varphi - 6(1+\mu)$$
$$\cos^4\varphi - 3(3+2\mu)\sin^2\varphi\cos^2\varphi + (1-2\mu)\sin^2\varphi + (2\mu-1)\cos^2\varphi)]\frac{1}{R^3}$$

$$\sigma_\theta = \{4[(2\mu-1)A_4]\cos\varphi\}R + \quad (1.2)$$
$$2[3\mu A_3 + (2\mu-1)A_5] + A_9[3(2\mu-1)\cos^2\varphi + (1-2\mu)]\frac{1}{R^3}$$

$$\sigma_\varphi = \{4[2\mu-1)A_4]\cos^3\varphi + 8[-8(1-\mu)A_2 + 2A_4]\sin^2\varphi\cos\varphi\}R + \quad (1.3)$$
$$\{2[3\mu A_3 + 2(\mu-1)A_5]\cos^2\varphi + 2[3(1-\mu)A_3 + 2(2-\mu)A_5]\sin^2\varphi\} +$$
$$A_9[3(2\mu-1)\cos^2\varphi + (1-2\mu)(\cos^2\varphi - \sin^2\varphi)]\frac{1}{R^3}$$

$$\tau_{R\varphi} = \quad 1.4$$
$$\{4[8(1-\mu)A_2 + (3\mu-5)A_4]\sin^2\varphi\cos^2\varphi - 4[8(1-\mu)A_2 - \mu A_4]\sin^3\varphi\}R +$$
$$[6(2\mu-1)A_3 + 2(4\mu-5)A_5]\sin\varphi\cos\varphi + 2A_9(1+\mu)\frac{1}{R^3}\sin\varphi\cos\varphi$$

$$A_2 = \frac{(6\mu-1)}{64(1-\mu)(1-2\mu)}\gamma$$

$$A_3 = -\frac{B_5}{6B_2}$$

$$A_4 = \frac{\mu}{4(1-\mu)(2\mu-1)}\gamma$$

$$A_5 = -\frac{B_6}{2B_2}$$

$$A_9 = -\frac{B_7}{B_2}$$

$$B_5 =$$
$$2(2\mu-1)h^3[(1-\mu)(2\mu-1)p_z + 2\mu(2-\mu)\gamma h][(2-\mu)\cos^2\varphi - (1+\mu)\sin^2\varphi] -$$
$$\mu(2\mu-1)R_1^3(p_z+\gamma h)[2(2-\mu)\cos^2\varphi + (2\mu-1)\sin^3\varphi]$$
$$[15\cos^7\varphi - 6(1+\mu)\cos^5\varphi + (2\mu-1)\cos^3\varphi] -$$
$$4\mu h^3(2-\mu)(2\mu-1)(p_z+\gamma h)[2(2-\mu)\cos^2\varphi - (1+\mu)\sin^2\varphi] +$$
$$(2\mu-1)R_1^3[15\cos^7\varphi - 6(1+\mu)\cos^5\varphi + (2\mu-1)\cos^3\varphi]$$
$$[(6\mu-1)(1-\mu)\gamma R_1\sin^2\varphi\cos\varphi - 2(2-\mu)R_1\gamma\cos^3\varphi + \mu R_1\gamma\sin^2\varphi\cos\varphi]$$
$$B_2 = (1-\mu)(2\mu-1)\{R_1^3(1-2\mu)[\mu\sin^2\varphi + (1-\mu)\cos^2\varphi]$$
$$[15\cos^7\varphi - 6(1+\mu)\cos^5\varphi + (2\mu-1)\cos^3\varphi] +$$

$$R_1^3\mu[2(2-\mu)\cos^2\varphi + (2\mu-1)\sin^2\varphi][15\cos^7\varphi - 6(1+\mu)\cos^5\varphi +$$
$$(2\mu-1)\cos^3\varphi] + 4\mu h^3(2-\mu)[2(2-\mu)\cos^2\varphi - (1+\mu)\sin^2\varphi] +$$
$$2h^3(1-\mu)(1-2\mu)[2(2-\mu)\cos^2\varphi - (1+\mu)\sin^2\varphi]\}$$

$$B_6 =$$
$$-2\mu h^3[(1-\mu)(2\mu-1)p_z + 2\mu(2-\mu)\gamma h][2(2-\mu)\cos^2\varphi - (1+\mu)\sin^2\varphi] +$$
$$\mu(2\mu-1)R_1^3(p_z+\gamma h)[\mu\sin^2\varphi + (1-\mu)\cos^2\varphi]$$
$$[15\cos^7\varphi - 6(1+\mu)\cos^5\varphi + (2\mu-1)\cos^3\varphi] + 2\mu h^3(1-\mu)(2\mu-1)p_z + \gamma h)$$
$$[2(2-\mu)\cos^2\varphi - (1+\mu)\sin^2\varphi] -$$
$$\mu[15\cos^7\varphi - 6(1+\mu)\cos^5\varphi + (2\mu-1)\cos^3\varphi]$$
$$[(6\mu-1)(1-\mu)R_1^4\gamma\sin^2\varphi\cos\varphi - 2(2-\mu)R_1^4\gamma\cos^3\varphi + \mu R_1^4\gamma\sin^2\varphi\cos\varphi]$$

$$B_7 = h^3\{[1-2\mu]$$
$$R_1^3[(1-\mu)(2\mu-1)p_z + 2\mu(2-\mu)\gamma h][\mu\sin^2\varphi + (1-\mu)\cos^2\varphi] +$$
$$\mu R_1^3[(1-\mu(2\mu-1)p_z + 2\mu(2-\mu)\gamma h][2(2-\mu)\cos^2\varphi + (2\mu-1)\sin^2\varphi] +$$
$$2\mu(2-\mu)(2\mu-1)R_1^3(p_z+\gamma h)[\mu\sin^2\varphi + (1-\mu)\cos^2\varphi] -$$
$$\mu(1-\mu)(2\mu-1)R_1^3(p_z+\gamma h)[2(2-\mu)\cos^2\varphi + (2\mu-1)\sin^2\varphi] -$$
$$2\mu(2-\mu)R_1^3[(6\mu-1)(1-\mu)\gamma R_1\sin^2\varphi\cos\varphi -$$
$$2(2-\mu)R_1\gamma\cos^3\varphi + \mu R_1\gamma\sin^2\varphi\cos\varphi] + (1-\mu)(2\mu-1)$$
$$R_1^3[(6\mu-1)(1-\mu)\gamma R_1\sin^2\varphi\cos\varphi - 2(2-\mu)R_1\gamma\cos^3\varphi + \mu R_1\gamma\sin^2\varphi\cos\varphi]\}$$

Related symbols in the formulas are defined as follows:
$p_z$—external load borne by the ground;
$\varphi$—vertical angle at a random point in the space, in rad;
$\gamma$—gravity density of rock-soil layer, in kN·m;
$\mu$—Poisson's ratio of rock-soil mass;
h—thickness of overlying stratum, in m;
R—distance from any point to spherical cavity center, in m.

The mathematical expressions in Step 3 are as follows:

$$p_{z3} = \frac{\sqrt{\left[\left[\frac{6\mu\gamma h(\mu^2-7\mu+1)}{(1+\mu)^2(1-\mu)^2(2\mu-1)} + \frac{8}{1-\mu}\text{ctan}\left(\frac{\pi}{4}+\frac{\varphi_1}{2}\right)\right]\right]^2 - \frac{12\mu(2-\mu)}{(1+\mu)^2(1-\mu)^2}\left[\frac{27\mu^2\gamma^2h^2}{(1+\mu)^2(1-\mu)^2(2\mu-1)} - 4\left[\frac{6\mu-1}{2(2\mu-1)}\gamma R_1 + \frac{\mu^2}{(1-\mu)(2\mu-1)}\gamma R_1\right]^2 - \frac{24\mu\gamma}{(1-\mu)(2\mu-1)}h c\tan\left(\frac{\pi}{4}+\frac{\varphi_1}{2}\right) + 16c^2\tan^2\left(\frac{\pi}{4}+\frac{\varphi_1}{2}\right)\right]} {\left(\frac{6\mu(2-\mu)}{(1+\mu)^2(1-\mu^2)}\right)}$$

(2.1)

$$p_{z4} = \left[\frac{6\mu\gamma h(\mu^2 - 7\mu + 1)}{(1+\mu)^2(1-\mu)^2(2\mu-1)} + \frac{8}{1-\mu}\operatorname{ctan}\left(\frac{\pi}{4} + \frac{\varphi_1}{2}\right)\right] - \sqrt{\left[\frac{6\mu\gamma(\mu^2 - 7\mu + 1)}{(1+\mu)^2(1-\mu)^2(2\mu-1)}h + \frac{8}{1-\mu}\operatorname{ctan}\left(\frac{\pi}{4} + \frac{\varphi_1}{2}\right)\right]^2 - \frac{12\mu(2-\mu)}{(1+\mu)^2(1-\mu)^2} \cdot \frac{27\mu^2\gamma^2 h^2}{(1+\mu)^2(1-\mu)^2(2\mu-1)} - 4\left[\frac{6\mu-1}{2(2\mu-1)}\gamma R_1 + \frac{\mu^2}{(1-\mu)(2\mu-1)}\gamma R_1\right]^2 - \frac{24\mu\gamma}{(1-\mu)(2\mu-1)}h c \tan\left(\frac{\pi}{4} + \frac{\varphi_1}{2}\right) + 16c^2\tan^2\left(\frac{\pi}{4} + \frac{\varphi_1}{2}\right)\right\}} \Bigg/ \frac{6\mu(2-\mu)}{(1+\mu)^2(1-\mu)^2}$$

(2.2)

Related symbols in the formulas are defined as follows:
φ$_1$—internal friction angle of rock-soil mass, in rad;
c—cohesion of rock-soil mass, in kPa;
γ—gravity density of overlying rock-soil layer on the top surface of columnar cavity, in kN·m;
μ—Poisson's ratio of rock-soil mass;
h—thickness of overlying stratum, in m;
R$_1$—sectional radius of a spherical cavity, in m.

The present disclosure is beneficial in:
The present disclosure provides a method for quantifying the bearing capacity of foundation containing shallow-hidden spherical cavities, which comprehensively considers a combined effect of spatial three-dimensional characteristics of a shallow-hidden spherical cavity, a self-weight stress of an overlying rock-soil layer, a virgin rock stress, and an external vertical load, and derives mathematical expressions for calculating the bearing capacity of roof. This method has many advantages such as comprehensive consideration, high accuracy and reliability of calculation results, and may provide the scientific basis for the development of prevention and control against the instability of the foundation containing shallow-hidden cavities. Parameters of rock-soil mass such as internal friction angle, cohesion, gravity density, and Poisson's ratio that are involved in the mathematical expressions may be obtained through field investigation and sampling, and by basic laboratory tests. Parameters such as geometric dimensions of the spherical cavity and thickness of the overlying rock-soil layer may be determined by comprehensively applying geophysical methods. This method is easy to operate and feasible to become popular in actual engineering projects.

DETAILED DESCRIPTION

Figure 1:
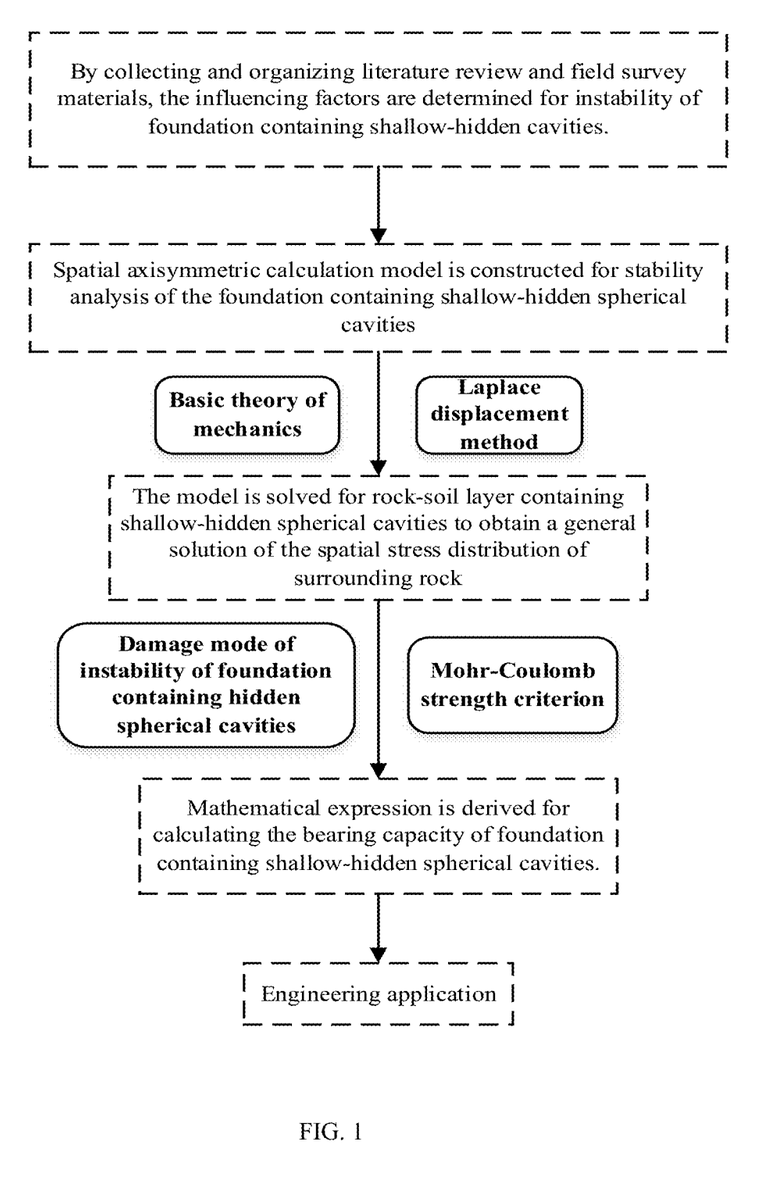
FIG. 1 is a process diagram of the method described according to the present disclosure.
Figure 2:
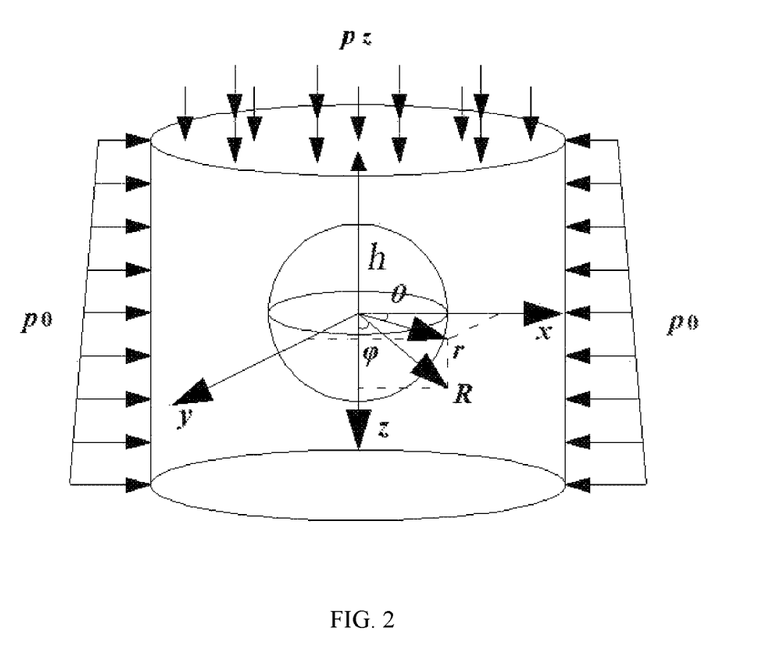
FIG. 2 is a schematic diagram of the calculation model described according to the present disclosure.
Figure 3:
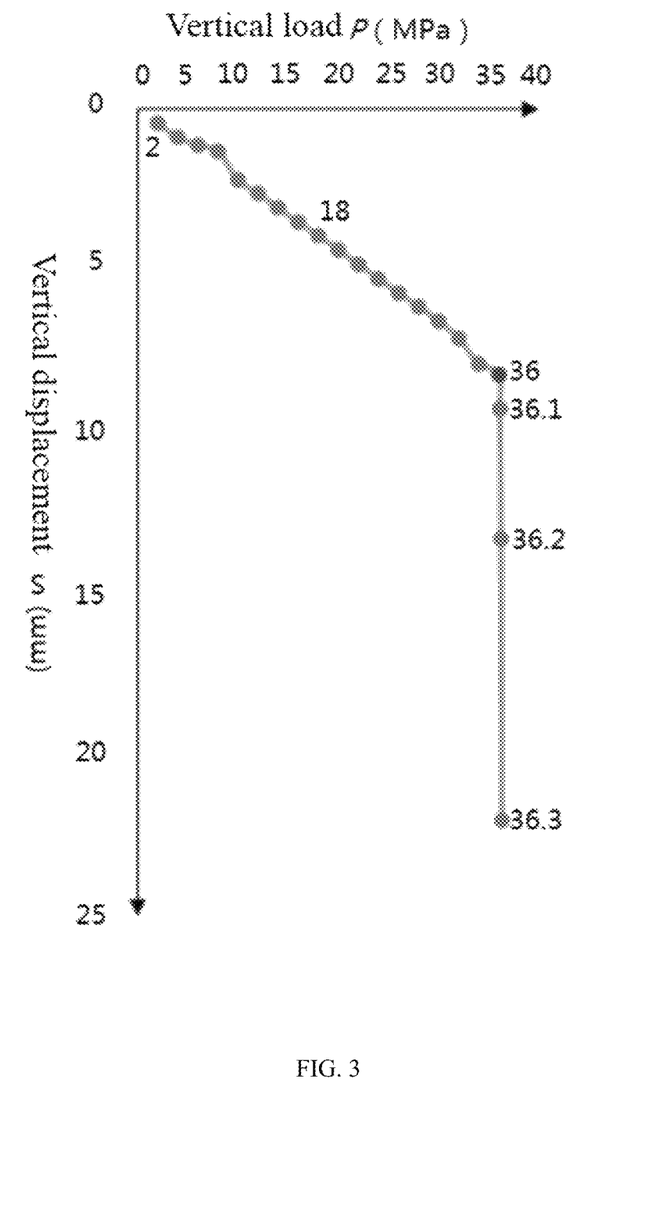
FIG. 3 is a schematic diagram of the P-S curve at the key point during the test according to the present disclosure.

Please refer to FIGS. 1-3, wherein:

The present disclosure provides a method for quantifying the bearing capacity of foundation containing shallow-hidden spherical cavities, including steps described as follows:

In Step 1, by comprehensively considering a combined effect of spatial three-dimensional characteristics of a shallow-hidden spherical cavity, a self-weight stress of an overlying rock-soil layer, a virgin rock stress, and an external vertical load, a spatial axisymmetric calculation model is constructed for stability analysis of the foundation containing shallow-hidden spherical cavities;

In Step 2, by selecting a spherical coordinate system and introducing the Laplace displacement method, the model is solved through theoretical analysis to obtain a general solution which reflects the spatial stress distribution of surrounding rock containing shallow-hidden spherical cavities;

In Step 3, by combining the general solution obtained through theoretical analysis in Step 2, a damage mode of ground collapse, and the Mohr-Coulomb strength theory, a mathematical expression for calculating the bearing capacity of the foundation containing shallow-hidden spherical cavities is derived;

In Step 4, by substituting data of a vertical load of stratum, a gravity density of a rock-soil layer, a Poisson's ratio of rock-soil mass, a thickness of an overlying stratum, and a radius of a spherical cavity that are measured in actual engineering projects into the mathematical expression in Step 3 for calculation, the bearing capacity of the foundation may be determined.

Various parameters and formulas in the spatial axisymmetric calculation model in Step 1 are as follows:
p$_z$—external load borne by the ground;
p$_0$—horizontal load of virgin rock stratum, p$_0$=μ[p$_z$+γ(h+z)]/(1−μ);
γ—gravity density of rock-soil layer, in kN·m;
μ—Poisson's ratio of rock-soil mass;
h—thickness of overlying stratum, in m;
R—distance from any point to spherical cavity center, in m.

The calculation formulas of the general solution in Step 2 are as follows:

$$\sigma_R = \{4[16(1-\mu)A_2 - A_4]\sin^2\varphi\cos\varphi + 8[(2-\mu)A_4]\cos^3\varphi\}R + \quad (1.1)$$
$$\{2[3\mu A_3 + (2\mu-1)A_5]\sin^2\varphi + 22[(1-\mu)A_3 + 2(2-\mu)A_5]\cos^2\varphi\} +$$
$$A_9\big[15\cos^6\varphi + 15\sin^4\varphi\cos\cos^2\varphi + 30^2\varphi\cos^4\varphi - 3\sin^4\varphi - 6(1+\mu)$$
$$\cos^4\varphi - 3(3+2\mu)\sin^2\varphi\cos^2\varphi + (1-2\mu)\sin^2\varphi + (2\mu-1)\cos^2\varphi\big]\frac{1}{R^3}$$

$$\sigma_\theta = \{4[(2\mu-1)A_4]\cos\varphi\}R + \quad (1.2)$$
$$2[3\mu A_3 + (2\mu-1)A_5] + A_9\big[3(2\mu-1)\cos^2\varphi + (1-2\mu)\big]\frac{1}{R^3}$$

$$\sigma_\varphi = \{4[2\mu-1)A_4]\cos^3\varphi + 8[-8(1-\mu)A_2 + 2A_4]\sin^2\varphi\cos\varphi\}R + \quad (1.3)$$
$$\{2[3\mu A_3 + 2(\mu-1)A_5]\cos^2\varphi + 2[3(1-\mu)A_3 + 2(2-\mu)A_5]\sin^2\varphi\} +$$
$$A_9\big[3(2\mu-1)\cos^2\varphi + (1-2\mu)(\cos^2\varphi - \sin^2\varphi)\big]\frac{1}{R^3}$$

$$\tau_{R\varphi} = \quad 1.4$$
$$\{4[8(1-\mu)A_2 + (3\mu-5)A_4]\sin^2\varphi\cos^2\varphi - 4[8(1-\mu)A_2 - \mu A_4]\sin^3\varphi\}R +$$
$$[6(2\mu-1)A_3 + 2(4\mu-5)A_5]\sin\varphi\cos\varphi + 2A_9(1+\mu)\frac{1}{R^3}\sin\varphi\sin\varphi$$

$$A_2 = \frac{(6\mu-1)}{64(1-\mu)(1-2\mu)}\gamma$$

$$A_3 = -\frac{B_5}{6B_2}$$

$$A_4 = \frac{\mu}{4(1-\mu)(2\mu-1)}\gamma$$

$$A_5 = -\frac{B_6}{2B_2}$$

$$A_9 = -\frac{B_7}{B_2}$$

$$B_5 =$$
$$2(2\mu-1)h^3[(1-\mu)(2\mu-1)p_z + 2\mu(2-\mu)\gamma h]\big[(2-\mu)\cos^2\varphi - (1+\mu)\sin^2\varphi\big] -$$
$$\mu(2\mu-1)R_1^3(p_z + \gamma h)\big[2(2-\mu)\cos^2\varphi + (2\mu-1)\sin^3\varphi\big]$$
$$\big[15\cos^7\varphi - 6(1+\mu)\cos^5\varphi + (2\mu-1)\cos^3\varphi\big] -$$
$$4\mu h^3(2-\mu)(2\mu-1)(p_z + \gamma h)\big[2(2-\mu)\cos^2\varphi - (1+\mu)\sin^2\varphi\big] +$$
$$(2\mu-1)R_1^3\big[15\cos^7\varphi - 6(1+\mu)\cos^5\varphi + (2\mu-1)\cos^3\varphi\big]$$
$$\big[(6\mu-1)(1-\mu)\gamma R_1\sin^2\varphi\cos\varphi - 2(2-\mu)R_1\gamma\cos^3\varphi + \mu R_1\gamma\sin^2\varphi\cos\varphi\big]$$

$$B_2 = (1-\mu)(2\mu-1)\{R_1^3(1-2\mu)\big[\mu\sin^2\varphi + (1-\mu)\cos^2\varphi\big]$$

-continued $$[15\cos^7\varphi - 6(1+\mu)\cos^5\varphi + (2\mu-1)\cos^3\varphi] +$$
$$R_1^3\mu[2(2-\mu)\cos^2\varphi + (2\mu-1)\sin^2\varphi][15\cos^7\varphi - 6(1+\mu)\cos^5\varphi +$$
$$(2\mu-1)\cos^3\varphi + 4\mu h^3(2-\mu)[2(2-\mu)\cos^2\varphi - (1+\mu)\sin^2\varphi] +$$
$$2h^3(1-\mu)(1-2\mu)[2(2-\mu)\cos^2\varphi - (1+\mu)\sin^2\varphi]\}$$

$$B_6 =$$
$$-2\mu h^3[(1-\mu)(2\mu-1)p_z + 2\mu(2-\mu)\gamma h][2(2-\mu)\cos^2\varphi - (1+\mu)\sin^2\varphi] +$$
$$\mu(2\mu-1)R_1^3(p_z+\gamma h)[\mu\sin^2\varphi + (1-\mu)\cos^2\varphi]$$
$$[15\cos^7\varphi - 6(1+\mu)\cos^5\varphi + (2\mu-1)\cos^3\varphi] + 2\mu h^3(1-\mu)(2\mu-1)p_z + \gamma h)$$
$$[2(2-\mu)\cos^2\varphi - (1+\mu)\sin^2\varphi] -$$
$$\mu[15\cos^7\varphi - 6(1+\mu)\cos^5\varphi + (2\mu-1)\cos^3\varphi]$$
$$[(6\mu-1)(1-\mu)R_1^4\gamma\sin^2\varphi\cos\varphi - 2(2-\mu)R_1^4\gamma\cos^3\varphi + \mu R_1^4\gamma\sin^2\varphi\cos\varphi]$$

$$B_7 = h^3\{[1-2\mu)$$

$$R_1^3[(1-\mu)(2\mu-1)p_z + 2\mu(2-\mu)\gamma h][\mu\sin^2\varphi + (1-\mu)\cos^2\varphi] +$$
$$\mu R_1^3[(1-\mu)(2\mu-1)p_z + 2\mu(2-\mu)\gamma h][2(2-\mu)\cos^2\varphi + (2\mu-1)\sin^2\varphi] +$$
$$2\mu(2-\mu)(2\mu-1)R_1^3(p_z+\gamma h)[\mu\sin^2\varphi + (1-\mu)\cos^2\varphi] -$$
$$\mu(1-\mu)(2\mu-1)R_1^3(p_z+\gamma h)[2(2-\mu)\cos^2\varphi + (2\mu-1)\sin^2\varphi] -$$
$$2\mu(2-\mu)R_1^3[(6\mu-1)(1-\mu)\gamma R_1\sin^2\varphi\cos\varphi -$$
$$2(2-\mu)R_1\gamma\cos^3\varphi + \mu R_1\gamma\sin^2\varphi\cos\varphi] + (1-\mu)(2\mu-1)$$
$$R_1^3[(6\mu-1)(1-\mu)\gamma R_1\sin^2\varphi\cos\varphi - 2(2-\mu)R_1\gamma\cos^3\varphi + \mu R_1\gamma\sin^2\varphi\cos\varphi]\}$$

Related symbols in the formulas are defined as follows:
$p_z$—external load borne by the ground;
φ—vertical angle at a random point in the space, in rad;
γ—gravity density of rock-soil layer, in kN·m;
μ—Poisson's ratio of rock-soil mass;
h—thickness of overlying stratum, in m;
R—distance from any point to spherical cavity center, in m.

The mathematical expressions in Step 3 are as follows:

$$p_{z3} = \left[\frac{6\mu\gamma h(\mu^2 - 7\mu + 1)}{(1+\mu)^2(1-\mu)^2(2\mu-1)} + \frac{8}{1-\mu}c\tan\left(\frac{\pi}{4} + \frac{\varphi_1}{2}\right)\right] + \frac{\sqrt{\left[\frac{6\mu\gamma(\mu^2-7\mu+1)}{(1+\mu)^2(1-\mu)^2(2\mu-1)}h + \frac{8}{1-\mu}c\tan\left(\frac{\pi}{4}+\frac{\varphi_1}{2}\right)\right]^2 - \frac{12\mu(2-\mu)}{(1+\mu)^2(1-\mu)^2} \cdot \frac{27\mu^2\gamma^2h^2}{(1+\mu)^2(1-\mu)^2(2\mu-1)} - 4\left[\frac{6\mu-1}{2(2\mu-1)}\gamma R_1 + \frac{\mu^2}{(1-\mu)(2\mu-1)}\gamma R_1\right]^2 - \frac{24\mu\gamma}{(1-\mu)(2\mu-1)}hc\tan\left(\frac{\pi}{4}+\frac{\varphi_1}{2}\right) + 16c^2\tan^2\left(\frac{\pi}{4}+\frac{\varphi_1}{2}\right)}}{\frac{6\mu(2-\mu)}{(1+\mu)^2(1-\mu)^2}} \quad (2.1)$$

$$p_{z4} = \left[\frac{6\mu\gamma h(\mu^2 - 7\mu + 1)}{(1+\mu)^2(1-\mu)^2(2\mu-1)} + \frac{8}{1-\mu}c\tan\left(\frac{\pi}{4} + \frac{\varphi_1}{2}\right)\right] - \frac{\sqrt{\left[\frac{6\mu\gamma(\mu^2-7\mu+1)}{(1+\mu)^2(1-\mu)^2(2\mu-1)}h + \frac{8}{1-\mu}c\tan\left(\frac{\pi}{4}+\frac{\varphi_1}{2}\right)\right]^2 - \frac{12\mu(2-\mu)}{(1+\mu)^2(1-\mu)^2} \cdot \frac{27\mu^2\gamma^2h^2}{(1+\mu)^2(1-\mu)^2(2\mu-1)} - 4\left[\frac{6\mu-1}{2(2\mu-1)}\gamma R_1 + \frac{\mu^2}{(1-\mu)(2\mu-1)}\gamma R_1\right]^2 - \frac{24\mu\gamma}{(1-\mu)(2\mu-1)}hc\tan\left(\frac{\pi}{4}+\frac{\varphi_1}{2}\right) + 16c^2\tan^2\left(\frac{\pi}{4}+\frac{\varphi_1}{2}\right)}}{\frac{6\mu(2-\mu)}{(1+\mu)^2(1-\mu)^2}} \quad (2.2)$$

Related symbols in the formulas are defined as follows:
$\varphi_1$—internal friction angle of rock-soil mass, in rad;
c—cohesion of rock-soil mass, in kPa;
$\gamma$—gravity density of overlying rock-soil layer on the top surface of columnar cavity, in kN·m;
$\mu$—Poisson's ratio of rock-soil mass;
h—thickness of overlying stratum, in m;
$R_1$—sectional radius of a spherical cavity, in m.

Implementations of the present disclosure will be further described with reference to figures and a certain engineering project below.

According to a preliminary survey report of a certain project, extremely thick limestone is the basic component among the survey field lithology. At the same time, the existence of spherical Karst caves identified by geophysical technologies such as drilling machines and geological radar also matches the research background of the present disclosure. According to relevant parameters provided in survey reports and interpretation results of 2D GPR (ground penetrating radar) images detected by field GPRs, physical and mechanical parameters of a study area are determined as shown in Table 1:

TABLE 1

Physical mechanical parameters of survey region

| Material | Natural gravity density (kg/m³) | Elasticity modulus (GPa) | Poisson's ratio | Internal friction angle (°) | Spherical radius (m) | Cohesion (MPa) | Internal filling pressure (MPa) |
|---|---|---|---|---|---|---|---|
| Limestone | 2650 | 35 | 0.25 | 42.3 | 0.5 | 7.8 | 0 |

By substituting related coefficients in Table 1 into (2.1)-(2.2), we get $p_z3=88.16$ MPa, and $p_z4=37.94$ MPa. By selecting a positive and smaller value as the roof bearing capacity, the roof bearing capacity is finally determined as 37.94 MPa.

As shown in FIG. 3, when the applied vertical load reaches 36 MPa and then increases by 0.1 MPa more, the vertical displacement of the key point will show a great abrupt change. On the other hand, it can be seen from the change of a plastic zone obtained by numerical simulation that the key point experienced a whole process: no plastic zone occurs at first, then both sides of the cave start to yield, and finally a sliding face is formed which reaches and penetrates through the ground. When the applied vertical load reaches 36 MPa, a sliding face penetrating the ground is also formed. By combining the above two conclusions comprehensively, 36 MPa at the abrupt change point is finally determined as the roof bearing capacity.

It can be seen from a comparison between the theoretical calculation results and the numerical simulation results that the calculation results of the two methods are quite consistent, and the numerical simulation results deviate within 5%, which are highly consistent.

What is claimed is:

1. A method for quantifying bearing capacity of foundation containing shallow-hidden spherical cavities, comprising:

step 1: constructing a spatial axisymmetric calculation model for stability analysis of the foundation containing shallow-hidden spherical cavities comprehensively including a combined effect of spatial three-dimensional characteristics of a shallow-hidden spherical cavity, a self-weight stress of an overlying stratum with thickness h a virgin rock stress comprising a horizontal load of a virgin rock stratum ($p_0$), and an external load borne by a ground ($p_z$);

step 2: selecting a spherical coordinate system and obtaining a general solution which reflects a spatial stress distribution of a surrounding rock containing shallow-hidden spherical cavities through theoretical analysis based on the spatial axisymmetric calculation model using a Laplace displacement method;

step deriving mathematical expressions for calculating the bearing capacity of the foundation containing shallow-hidden spherical cavities by combining the general solution obtained through the theoretical analysis in step 2, a damage mode of ground collapse, and a Mohr-Coulomb strength theory;

step 4: determining the bearing capacity of the foundation by substituting data of a vertical load of stratum, a gravity density of a rock-soil layer, a Poisson's ratio of rock-soil mass, a thickness of an overlying stratum, and a radius of a spherical cavity that are measured into the mathematical expressions in step 3 for calculation.

2. The method according to claim 1, wherein: the spatial axisymmetric calculation model in step 1 and related parameters are as follows:

$p_z$—the external load borne by the ground;
$p_0$—the horizontal load of the virgin rock stratum, $p_0=\mu[p_z+\gamma(h+z)]/1-\mu)$;
$\gamma$—the gravity density of the rock-soil layer, in kN/m³;
$\mu$—the Poisson's ratio of the rock-soil mass;
h—the thickness of the overlying stratum, in m;
R—a distance from any point to a spherical cavity center, in m.

3. The method according to claim 1, wherein: calculation formulas of the general solution in step 2 are as follows:

$$\sigma_R = \{4[16(1-\mu)A_2 - A_4]\sin^2\varphi\cos\varphi + 8[(2-\mu)A_4]\cos^3\varphi\}R + \\ \{2[3\mu A_3 + (2\mu-1)A_5]\sin^2\varphi + 22[(1-\mu)A_3 + 2(2-\mu)A_5]\cos^2\varphi\} + \\ A_9[15\cos^6\varphi + 15\sin^4\varphi\cos\cos^2\varphi + 30^2\varphi\cos\sin^4\varphi - 3\sin^4\varphi - 6(1+\mu) \\ \cos^4\varphi - 3(3+2\mu)\sin^2\varphi\cos^2\varphi + (1-2\mu)\sin^2\varphi + (2\mu-1)\cos^2\varphi)]\frac{1}{R^3} \quad (1.1)$$

$$\sigma_\theta = \{4[(2\mu-1)A_4]\cos\varphi\}R + \\ 2[3\mu A_3 + (2\mu-1)A_5] + A_9[3(2\mu-1)\cos^2\varphi + (1-2\mu)]\frac{1}{R^3} \quad (1.2)$$

$$\sigma_\varphi = \{4[2\mu-1)A_4]\cos^3\varphi + 8[-8(1-\mu)A_2 + 2A_4]\sin^2\varphi\cos\varphi\}R + \\ \{2[3\mu A_3 + 2(\mu-1)A_5]\cos^2\varphi + 2[3(1-\mu)A_3 + 2(2-\mu)A_5]\sin^2\varphi\} + \\ A_9[3(2\mu-1)\cos^2\varphi + (1-2\mu)(\cos^2\varphi)]\frac{1}{R^3} \quad (1.3)$$

-continued $$\tau_{R\varphi} = \{4[8(1-\mu)A_2 + (3\mu-5)A_4]\sin^2\varphi\cos^2\varphi - 4[8(1-\mu)A_2 - \mu A_4]\sin^3\varphi\}R +$$
$$[6(2\mu-1)A_3 + 2(4\mu-5)A_5]\sin\varphi\cos\varphi + 2A_9(1+\mu)\frac{1}{R^3}\sin\varphi\cos\varphi$$

(1.4)

$$A_2 = \frac{(6\mu-1)}{64(1-\mu)(1-2\mu)}\gamma$$

$$A_3 = -\frac{B_5}{6B_2}$$

$$A_4 = \frac{\mu}{4(1-\mu)(2\mu-1)}\gamma$$

$$A_5 = -\frac{B_6}{2B_2}$$

$$A_9 = -\frac{B_7}{B_2}$$

$$B_5 = 2(2\mu-1)h^3[(1-\mu)(2\mu-1)p_z + 2\mu(2-\mu)\gamma h][(2-\mu)\cos^2\varphi - (1+\mu)\sin^2\varphi] -$$
$$\mu(2\mu-1)R_1^3(p_z + \gamma h)[2(2-\mu)\cos^2\varphi + (2\mu-1)\sin^2\varphi][$$
$$15\cos^7\varphi - 6(1+\mu)\cos^5\varphi + (2\mu-1)\cos^3\varphi] -$$
$$4\mu h^3(2-\mu)(2\mu-1)(p_z + \gamma h)[2(2-\mu)\cos^2\varphi - (1+\mu)\sin^2\varphi] +$$
$$(2\mu-1)R_1^3[15\cos^7\varphi - 6(1+\mu)\cos^5\varphi + (2\mu-1)\cos^3\varphi][$$
$$(6\mu-1)(1-\mu)\gamma R_1\sin^2\varphi\cos\varphi - 2(2-\mu)R_1\gamma\cos^3\varphi + \mu R_1\gamma\sin^2\varphi\cos\varphi]$$

$$B_2 = (1-\mu)(2\mu-1)\{R_1^3(1-2\mu)[\mu\sin^2\varphi + (1-\mu)\cos^2\varphi][$$
$$15\cos^7\varphi - 6(1+\mu)\cos^5\varphi + (2\mu-1)\cos^3\varphi] +$$
$$R_1^3\mu[2(2-\mu)\cos^2\varphi + (2\mu-1)\sin^2\varphi][15\cos^7\varphi - 6(1+\mu)\cos^5\varphi +$$
$$(2\mu-1)\cos^3\varphi + 4\mu h^3(2-\mu)[2(2-\mu)\cos^2\varphi - (1+\mu)\sin^2\varphi] +$$
$$2h^3(1-\mu)(1-2\mu)[2(2-\mu)\cos^2\varphi - (1+\mu)\sin^2\varphi]\}$$

$$B_6 = -2\mu h^3[(1-\mu)(2\mu-1)p_z + 2\mu(2-\mu)\gamma h][2(2-\mu)\cos^2\varphi - (1+\mu)\sin^2\varphi] +$$
$$\mu(2\mu-1)R_1^3(p_z + \gamma h)[\mu\sin^2\varphi + (1-\mu)\cos^2\varphi][$$
$$15\cos^7\varphi - 6(1+\mu)\cos^5\varphi + (2\mu-1)\cos^3\varphi] +$$
$$2\mu h^3(1-\mu)(2\mu-1)p_z + \gamma h)[2(2-\mu)\cos^2\varphi - (1+\mu)\sin^2\varphi] -$$
$$\mu[15\cos^7\varphi - 6(1+\mu)\cos^5\varphi + (2\mu-1)\cos^3\varphi][$$
$$(6\mu-1)(1-\mu)R_1^4\gamma\sin^2\varphi\cos\varphi -$$
$$2(2-\mu)R_1^4\gamma\cos^3\varphi + \mu R_1^4\gamma\sin^2\varphi\cos\varphi]$$

$$B_7 = h^3\{[1-2\mu]$$
$$R_1^3[(1-\mu)(2\mu-1)p_z + 2\mu(2-\mu)\gamma h][\mu\sin^2\varphi + (1-\mu)\cos^2\varphi] +$$
$$\mu R_1^3[(1-\mu(2\mu-1)p_z + 2\mu(2-\mu)\gamma h][2(2-\mu)\cos^2\varphi + (2\mu-1)\sin^2\varphi] +$$
$$2\mu(2-\mu)(2\mu-1)R_1^3(p_z + \gamma h)[\mu\sin^2\varphi + (1-\mu)\cos^2\varphi] -$$
$$\mu(1-\mu)(2\mu-1)R_1^3(p_z + \gamma h)[2(2-\mu)\cos^2\varphi + (2\mu-1)\sin^2\varphi] -$$
$$2\mu(2-\mu)R_1^3[(6\mu-1)(1-\mu)\gamma R_1\sin^2\varphi\cos\varphi -$$
$$2(2-\mu)R_1\gamma\cos^3\varphi + \mu R_1\gamma\sin^2\varphi\cos\varphi] + (1-\mu)(2\mu-1)$$
$$R_1^3[(6\mu-1)(1-\mu)\gamma R_1\sin^2\varphi\cos\varphi - 2(2-\mu)R_1\gamma\cos^3\varphi + \mu R_1\gamma\sin^2\varphi\cos\varphi]\}$$

where symbols in the calculation formulas are defined as follows:

$p_z$—the external load borne by the ground;
φ—a vertical angle at a random point in a space, in rad;
γ—gravity density of the rock-soil layer, in $kN/m^3$;
μ—the Poisson's ratio of rock-soil mass;
h—the thickness of the overlying stratum, in m;
R—a distance from any point to a spherical cavity center, in m.

4. The method according to claim 1, wherein: the mathematical expressions in step 3 are as follows to obtain two positive values $p_{z3}$ and $p_{z4}$, and one smaller value of the two positive values is selected as the bearing capacity of the foundation:

$$p_{z3} = \left[\frac{6\mu\gamma h(\mu^2 - 7\mu + 1)}{(1+\mu)^2(1-\mu)^2(2\mu-1)} + \frac{8}{1-\mu}c\tan\left(\frac{\pi}{4} + \frac{\varphi_1}{2}\right)\right] + \sqrt{\left[\frac{6\mu\gamma(\mu^2-7\mu+1)}{(1+\mu)^2(1-\mu)^2(2\mu-1)}h + \frac{8}{1-\mu}c\tan\left(\frac{\pi}{4}+\frac{\varphi_1}{2}\right)\right]^2 - \frac{12\mu(2-\mu)}{(1+\mu)^2(1-\mu)^2} \cdot \frac{27\mu^2\gamma^2 h^2}{(1+\mu)^2(1-\mu)^2(2\mu-1)} - 4\left[\frac{6\mu-1}{2(2\mu-1)}\gamma R_1 + \frac{\mu^2}{(1-\mu)(2\mu-1)}\gamma R_1\right]^2 - \frac{24\mu\gamma}{(1-\mu)(2\mu-1)}hc\tan\left(\frac{\pi}{4}+\frac{\varphi_1}{2}\right) + 16c^2\tan^2\left(\frac{\pi}{4}+\frac{\varphi_1}{2}\right)} \bigg/ \frac{6\mu(2-\mu)}{(1+\mu)^2(1-\mu)^2} \qquad (2.1)$$

$$p_{z4} = \left[\frac{6\mu\gamma h(\mu^2 - 7\mu + 1)}{(1+\mu)^2(1-\mu)^2(2\mu-1)} + \frac{8}{1-\mu}c\tan\left(\frac{\pi}{4} + \frac{\varphi_1}{2}\right)\right] - \sqrt{\left[\frac{6\mu\gamma(\mu^2-7\mu+1)}{(1+\mu)^2(1-\mu)^2(2\mu-1)}h + \frac{8}{1-\mu}c\tan\left(\frac{\pi}{4}+\frac{\varphi_1}{2}\right)\right]^2 - \frac{12\mu(2-\mu)}{(1+\mu)^2(1-\mu)^2} \cdot \frac{27\mu^2\gamma^2 h^2}{(1+\mu)^2(1-\mu)^2(2\mu-1)} - 4\left[\frac{6\mu-1}{2(2\mu-1)}\gamma R_1 + \frac{\mu^2}{(1-\mu)(2\mu-1)}\gamma R_1\right]^2 - \frac{24\mu\gamma}{(1-\mu)(2\mu-1)}hc\tan\left(\frac{\pi}{4}+\frac{\varphi_1}{2}\right) + 16c^2\tan^2\left(\frac{\pi}{4}+\frac{\varphi_1}{2}\right)} \bigg/ \frac{6\mu(2-\mu)}{(1+\mu)^2(1-\mu)^2} \qquad (2.2)$$

where symbols in the mathematical expressions are defined as follows:

$\varphi_1$—an internal friction angle of the rock-soil mass, in rad;

c—cohesion of the rock-soil mass, in kPa;

$\gamma$—gravity density of the overlying rock-soil layer on a top surface of a columnar cavity, in kN/m³;

$\mu$—the Poisson's ratio of the rock-soil mass;

h—the thickness of the overlying stratum, in m; and $R_1$—sectional radius of the shallow-hidden spherical cavity, in m.

\* \* \* \* \*